United States Patent [19]
Adams et al.

[11] Patent Number: 5,372,605
[45] Date of Patent: Dec. 13, 1994

[54] DUAL BATTERY POWER SYSTEM FOR AN IMPLANTABLE CARDIOVERTER DEFIBRILLATOR

[75] Inventors: Theodore P. Adams, Edina; Dennis A. Brumwell, Bloomington; Joseph S. Perttu, Chanhassen; Charles G. Supino, Arden Hills, all of Minn.

[73] Assignee: Angeion Corporation, Plymouth, Minn.

[21] Appl. No.: 108,130

[22] Filed: Aug. 16, 1993

Related U.S. Application Data

[63] Continuation-in-part of Ser. No. 913,626, Jul. 16, 1992, Pat. No. 5,235,979.

[51] Int. Cl.$^5$ ............................................. A61N 1/39
[52] U.S. Cl. .......................................... 607/5; 607/34; 607/29
[58] Field of Search ........................... 607/5, 29, 34

[56] References Cited

U.S. PATENT DOCUMENTS

| | | |
|---|---|---|
| 4,134,408 | 1/1979 | Brownlee et al. |
| 4,323,075 | 4/1982 | Langer . |
| 4,345,604 | 8/1982 | Renirie . |
| 4,416,282 | 11/1983 | Saulson et al. |
| 4,548,209 | 10/1985 | Wielders et al. |

*Primary Examiner*—William E. Kamm
*Assistant Examiner*—Kennedy J. Schaetzle
*Attorney, Agent, or Firm*—Patterson & Keough

[57] ABSTRACT

An improved dual battery power system uses two separate battery power sources for an implantable cardioverter defibrillator, each having optimized characteristics for monitoring functions and for output energy delivery functions, respectively. The monitoring functions are supplied electrical power by a first battery source, such as a conventional pacemaker power source in the form of a lithium iodide battery which is optimized for long life at very low current levels. The output energy delivery functions are supplied by a separate second battery source, such as a pair of lithium vanadium pentoxide batteries, which is optimized for high current drain capability and low self-discharge for long shelf life. The first battery source provides electrical power only to the monitoring functions of the implantable cardioverter defibrillator, and the second battery source provides all of the electrical power for the output energy delivery functions.

8 Claims, 7 Drawing Sheets

DUAL BATTERY POWER SYSTEM FOR AN IMPLANTABLE CARDIOVERTER DEFIBRILLATOR

RELATED APPLICATIONS

This application is a continuation-in-part application of an application filed in the United States Patent and Trademark Office on Jul. 16, 1992, entitled DUAL BATTERY SYSTEM FOR IMPLANTABLE DEFIBRILLATOR, Ser. No. 07/913,626, now U.S. Pat. No. 5,235,979 which is a file-wrapper continuation of an application by the same title filed on Mar. 3, 1991, both of which are assigned to the assignee of the present invention, and the disclosure of which is incorporated by reference in the present application- This application is related to a co-pending application filed in the United States Patent and Trademark Office on Mar. 15, 1993, entitled IMPLANTABLE CARDIOVERTER DEFIBRILLATOR HAVING A SMALLER DISPLACEMENT VOLUME, Ser. No. 08/033,632, which is assigned to the assignee of the present invention and the disclosure of which is hereby incorporated in the present application.

BACKGROUND OF THE INVENTION

1. Field of the Invention

The present invention pertains to a cardioverter defibrillator, and more particularly, to an improved dual battery power system for use with an implantable cardioverter defibrillator.

2. Background of the Invention

Implantable cardioverter defibrillators have several unique battery requirements, as compared to other implantable products. An implantable cardioverter defibrillator demands a battery with the following general characteristics: very high reliability, highest possible energy density (i.e., small size), extremely low self-discharge rating (i.e., long shelf life), very high current capability, high operating voltage, and high sealability (i.e., no gas or liquid venting).

Some of these parameters have some measure of mutual exclusivity, making it difficult to optimize the battery or electronics without making compromises to the design of the implantable device. In its monitoring mode, the implantable cardioverter defibrillator requires the battery to deliver continuous currents in the range of only 10-30 $\mu$A, while in its defibrillation mode, the same battery must deliver currents in the range of one to two amps, some five orders of magnitude greater than the current required for the monitoring mode.

Presently, all manufactured implantable cardioverter defibrillators use a single battery system to power the implantable device. The longevity of an implanted cardioverter defibrillator with a single battery configuration and the number of shocks the defibrillator is capable of delivering are strictly dependant on the remaining battery capacity at any given time. As the device ages, its ability to deliver an adequate number of defibrillating shocks declines as the battery is depleted by the monitoring electronics. Similarly, if a patient receives a large number of shocks soon after implant, the remaining monitoring life is reduced. Thus, it is difficult to assess the condition of the battery and its remaining useful life after it has been in use for a period of time.

A further disadvantage of the single battery configuration is that the ideal voltage requirements for the monitoring and output functions are opposite. For the monitoring function, it is desirable to use the lowest possible voltage that the circuits can operate reliably with in order to conserve energy. This is typically in the order of 1.5-3.0 V. On the other hand, the output circuit works most efficiently with the highest possible battery voltage in order to produce firing voltages of up to about 750 V.

All existing manufactured implantable cardioverter defibrillators have compromised between these two demands by using a single battery system or configuration which is typically comprised of two lithium silver vanadium pentoxide cells electrically connected in series to produce an output battery voltage of about 6 V. The battery voltage must be elevated via an inverter circuit to the firing voltage of about 750 V. The net result is that power is wasted in both the monitoring and output circuits because the monitoring circuit which requires only 2-3 V must operate from a relatively high 6 V source, and the output circuit whose efficiency is a function of the supply voltage must operate from the relatively low 6 V source.

At least two previous development attempts have been made to avoid some of the problems inherent in using a single battery system configuration for an implantable cardioverter defibrillator. In the Medtronic Model 2315, lithium thionyl chloride batteries were employed for the high-voltage charging circuit and lithium manganese dioxide batteries were used for the remaining low voltage circuitry. Similarly, the Telectronics Model 4201 initially tried to employ separate batteries for the low voltage circuits (lithium iodine) and high-voltage circuits (lithium silver vanadium pentoxide). Troop, P. J., "Implantable Cardioverters and Defibrillators", *Current Problems in Cardiology*, Vol. XIV, No. 12, (December 1989), pp. 703-04. Unfortunately, neither of these devices resulted in practical, manufactured implantable cardioverter defibrillators and the dual battery approach was abandoned in both cases.

While single battery systems have proved workable for implantable cardioverter defibrillators, the use of a single battery system necessarily involves a compromise between the ideal power supplies which would otherwise be used for the various types of circuitry within the implantable cardioverter defibrillator. Accordingly, it would be desirable to provide for an improved dual battery power system for an implantable cardioverter defibrillator which avoids the need for the compromises required of single battery systems, and which overcomes the problems of earlier attempts at dual battery systems.

SUMMARY OF THE INVENTION

An improved dual battery power system in accordance with the present invention involves the use of two separate battery power sources for an implantable cardioverter defibrillator, each having optimized characteristics for monitoring functions and for output energy delivery functions, respectively. The monitoring functions are supplied electrical power by a first battery source, such as a conventional pacemaker power source in the form of a lithium iodide battery cell which is optimized for long life at very low current levels. The output energy delivery functions are supplied by a separate second battery source, such as a pair of lithium vanadium pentoxide battery cells, which is optimized for high current drain capability and low self-discharge for long shelf life. The first battery source provides electrical power only to the monitoring functions of the implantable cardioverter defibrillator, and the second battery source provides all of the electrical power for the output energy delivery functions.

With the improved dual battery system configuration of the present invention, the minimum expected monitoring life of an implantable cardioverter defibrillator is independent of the amount of electrical pulse therapy delivered by the device, such as the number of cardioversion/defibrillation countershocks or the amount of pacing. As a result, the end of the minimum useable lifespan of the first battery source is highly predictable based on steady state current drain calculations. The lifespan of the second source battery source is also amenable to calculation based upon the number and amount of energy levels of previously delivered electrical pulse therapies.

The major advantage of the present invention is that each battery source voltage can be optimized for the particular circuit wherein it is used. The first battery source is preferably a relatively low current, low voltage source, from 1.5 to 3.0 V typically; whereas the second battery source is preferably comprised of as high of a current and voltage as battery chemistry and battery packaging efficiencies allow, typically ranging from 6 to 18 V.

Unlike existing implantable cardioverter defibrillators, a preferred embodiment of the present invention utilizes a separate hardware-based, low-power monitoring circuitry to monitor for certain wake-up conditions which will then activate the output delivery circuitry which includes a microprocessor that performs further detection and, if necessary, selects an appropriate cardioversion/defibrillation therapy to be delivered. The output delivery circuitry includes additional hardware circuitry that, when enabled, can delivery pacing therapy pulses with energy supplied from the output power source battery without the need to wake the microprocessor.

Because the two batteries of the present invention can be optimized for their particular functions, different assumptions about the total energy requirements of the implantable cardioverter defibrillator can be made. For example, all existing manufactured implantable cardioverter defibrillators provide power systems which are designed to supply an initial number of defibrillation countershocks of at least 250 shocks. In a single battery system, even when no shocks are delivered, the number of remaining shocks in the device decreases with age due to the fact that the energy for the monitoring functions are drawn from this battery. In the present invention, assuming good charge retention of the output battery, essentially no energy is drawn from the output battery until an electrical pulse therapy is delivered. Consequentially, one advantage of the dual battery system of the present invention is that a smaller initial number of defibrillation countershocks can be specified for an implanted device, while maintaining the same minimum expected life span for the device, thereby allowing a reduction in the overall size of the implanted device.

Another advantage of a preferred embodiment of the present invention includes a backup protection feature whereby energy from the output power source battery can be used to power the monitoring circuitry in the event that the monitoring power source battery ceases to function. A further advantage of a preferred embodiment of the present invention includes a booster feature which regulates the system supply voltage to prevent ripple in the supply voltage during capacitor charging. Still another advantages include a greater longevity provided for by lower energy drain by the monitoring circuitry, the simplified circuit design that results in a decrease in the risk of high internal currents causing interference to other parts of the low current monitoring and control circuitry, and the ability to use rechargeable batteries.

DESCRIPTION OF THE PREFERRED EMBODIMENT

Figure 1:
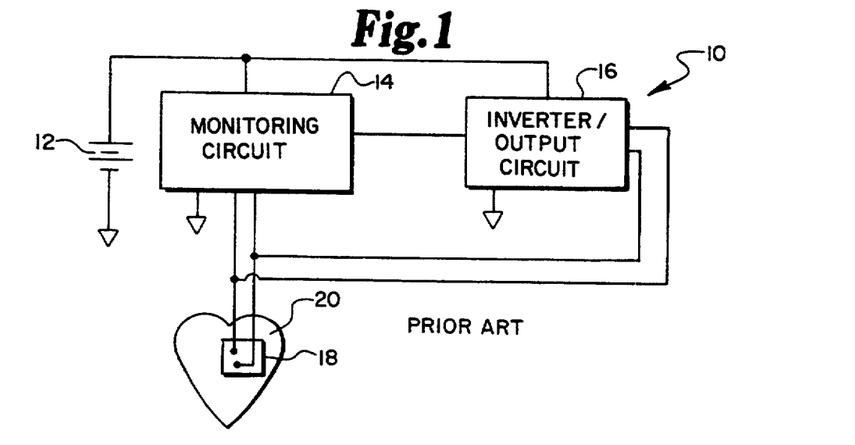
FIG. 1 illustrates a block diagram of a single battery system for an implantable cardioverter defibrillator.

FIG. 1 illustrates a single battery system for an implantable defibrillator system 10 including a single battery 12, which provides power both to a monitoring circuit 14 and an inverter/output circuit 16 simultaneously. The monitoring circuit 14 and the inverter/output circuit 16 are interconnected to each other, and to two or more implanted electrodes 18 located on, near or in a heart 20. The implanted electrodes 18 include appropriate leads and sensors to monitor the electrical activity of the heart 20 and to deliver an appropriate electrical therapy to the heart 20 in the event that the monitoring circuit detects a cardiac arrhythmia. As discussed in the background of the invention, the electrical capacity of the single battery 12 may be excessive in relation to the circuit requirements of the monitoring circuit 14, and marginal or even somewhat lacking in electrical size in relation to the circuit requirements of the inverter/output circuit 16.

Figure 2:
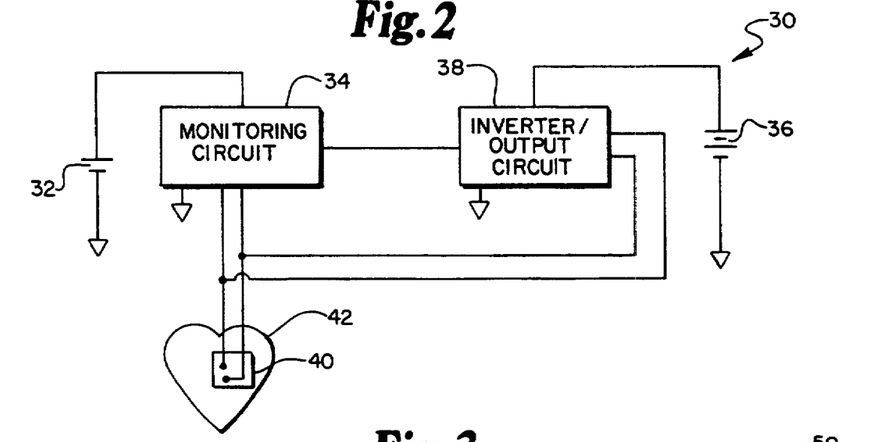
FIG. 2 illustrates a block diagram of the dual battery system of the present invention for an implantable cardioverter defibrillator.

FIG. 2 illustrates a block diagram of the dual battery system 30 for an implantable defibrillator of a preferred embodiment of the present invention. A battery 32 of appropriate voltage and physical size connects to and powers a monitoring circuit 34 only. Another battery 36 of appropriate voltage and physical size connects to and powers the inverter/output circuit 38 only. The monitoring circuit 34 and the inverter/output circuit 38 each connect to two or more implanted electrodes 40 on, near or in a heart 42. The monitoring circuit 34 also connects to and triggers the inverter/output circuit 38. The batteries 32 and 36 are optimally sized electrically and physically to provide for the most efficient operation for their respective circuitry.

Figure 3:
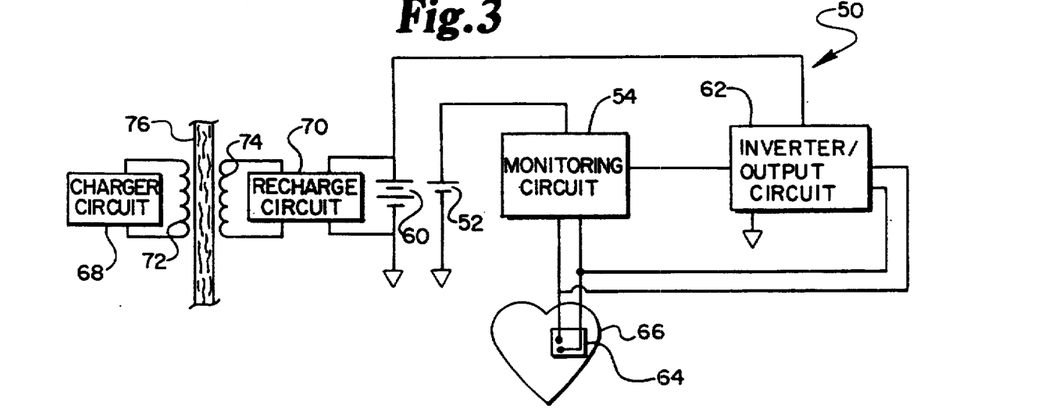
FIG. 3 illustrates a block diagram of the dual battery system of the present invention using a rechargeable inserter/output battery.

FIG. 3 illustrates a dual battery system 50 for an implantable defibrillator of an alternate embodiment of the present invention where the batteries are rechargeable. A battery 52 of appropriate voltage and physical size connects to and powers a monitoring circuit 54 only. Another battery 60, which is rechargeable and of appropriate voltage and physical size connects to and powers the inverter/output circuit 62 only. Charging of the battery 60 occurs by a radio frequency inductive link between an external charger circuit 68 and an implanted recharge circuit 70 that includes a rectifier. A coil 72 connects with the external charger circuit 68 and transmits RF energy from the coil 72 through the epidermis 76 where it is received by an implanted coil 74. The coil 74 supplies RF energy to the recharge circuit 70 so that the battery 60 may be charged.

In operation, as in FIG. 2, the monitoring circuit 54 and the inverter/output circuit 62 each connect to two or more implanted electrodes 64 on, in or near a heart 66. The monitoring circuit 54 also connects to and triggers the inverter/output circuit 62. The batteries 52 and 60 are optimally sized electrically and physically to provide for the most efficient operation. In this configuration, the device has a finite and predictable monitoring life based upon the capacity of the primary monitoring battery 52, and an infinite life for the output power surface battery 60 based on a theoretically perfect secondary rechargeable battery that only needed to be recharged after a predetermined number of electrical pulse therapies were delivered. Optionally, the battery 52 which powers the monitoring circuit 54 can also be rechargeable and would also include another similar RF inducutive charging link as used for the rechargeable batter 60.

A preferred mode of operation of the implantable cardioverter defibrillator shown in FIG. 2 is dependent upon the monitoring circuit 34 and the inverter/output circuit 38. In the event that the monitoring circuit 34 detects a wake-up condition, for example, the monitoring circuit 34 wakes up a microprocessor-based circuit in the inverter/output circuit 38 to respond to the wake-up condition. In the event that the monitoring circuit 34 is programmably enabled for pacing detection, and the monitoring circuit 34 detects a pacing condition, the monitoring circuit enables a hardware-based pacing circuit portion of the inverter/output circuit 38 to deliver a pacing pulse using energy from the battery 36. It will be noted that many different variations in conditions detected by the monitoring circuit 34 and types of responses provided by the inverter/output circuit 38 are possible, and it is intended that such combinations are within the scope of the present invention.

In one embodiment, a microprocessor with an RC gated oscillator circuit that is controlled by the microprocessor within the inverter/output circuit 38 implements a wake-up control that can respond to the wake-up conditions. The wake-up conditions handled by the microprocessor based circuit in the inverter/output circuit 38 include, for example, a tachycardia threshold determination, a telemetry indication, or a timer condition. In the case of the tachycardia threshold determination, for example, threshold determination circuitry in the monitoring circuit 34 detects the occurrence of 3 consecutive R-waves at a rate faster than a predetermined programmable rate. In response, the monitoring circuit 34 wakes-up the microprocessor in the inverter/output circuit 38, which verifies that a cardiac arrhythmia is occurring and selects an appropriate electrical pulse therapy. If an electrical pulse therapy is to be delivered, the battery 36 would charge the inverter/output circuit 38 to deliver one or more high voltage cardioversion/defibrillation countershocks. If the wake-up condition was a telemetry indication, then the microprocessor circuit of the inverter/output circuit 38 might "output" a telemetry response, for example, rather than a electrical pulse therapy response. Alternatively, if the microprocessor circuit of the inverter/output circuit 38 determines that no action is required in response to the wake-up condition, then no "output" may be generated in response and the microprocessor would turn off the RC gated oscillator circuit, thereby shutting off the clock to the microprocessor.

One important feature which distinguishes the improved dual battery system 30 from the previous attempts to implement dual battery systems is that the division of labor between the battery 32 and the battery 36 is not based on low voltage output vs. high voltage output, but rather is based on monitoring functions vs. output functions. In the two dual battery systems described in the background art section, all of the low voltage circuitry of the implantable cardioverter defibrillator was powered from a low voltage battery. As a result, both the monitoring function (which typically operate on 3 V levels), as well as the pacing therapy output functions (which typically operate on 6 V levels), were designed to derive their energy from the low voltage battery. The end result of this type of arrangement is that the life of the low voltage battery is totally dependant upon the amount of pacing therapy which may be delivered by the device and, thus, the minimum effective life of the device is effectively unknown.

In contrast, the improved dual battery power system of the present invention takes all of its "output" energy from the output battery 32. For example, the present invention does not take the energy for pacing therapy from the monitoring battery 32, but rather from the output battery 36. As a result, the monitoring lifespan of an implantable defibrillator in accordance with the present invention is known and calculable based on the specifications of the monitoring battery 32. Without a known lifespan of the device, it is simply not possible to provide a viable implantable defibrillator, as evidenced by the fact that both of the previous attempts at dual battery systems which did not have known lifespans for the monitoring circuitry were unsuccessful and did not result in manufactured implantable cardioverter defibrillators.

Referring now to FIGS. 4a-4e, a relative comparison between the electrical pulse therapy outputs and the longevity of the implantable cardioverter defibrillator is shown under various assumptions for a single battery system 100 and the improved dual battery system 102 of the present invention. One of the advantages of the present invention is that a smaller initial number of countershocks is required in order for the implantable cardioverter defibrillator to have the same minimum effective life span as a device with a single battery power system. This, in turn, decreases the overall power requirements, and, hence, the total size of the implantable cardioverter defibrillator. In the preferred embodiment, an additional advantage of having a more optimum discharge capacitor system in the implantable cardioverter defibrillator of a preferred embodiment also reduces the overall power requirements for the dual battery system of the present invention. For a more detailed explanation of the relationship between the therapies provided by the device and the power requirements and size of the device in the preferred embodiment, reference is made to the previously identified copending application entitled IMPLANTABLE CARDIOVERTER DEFIBRILLATOR HAVING A SMALLER DISPLACEMENT VOLUME.

Figure 4A:
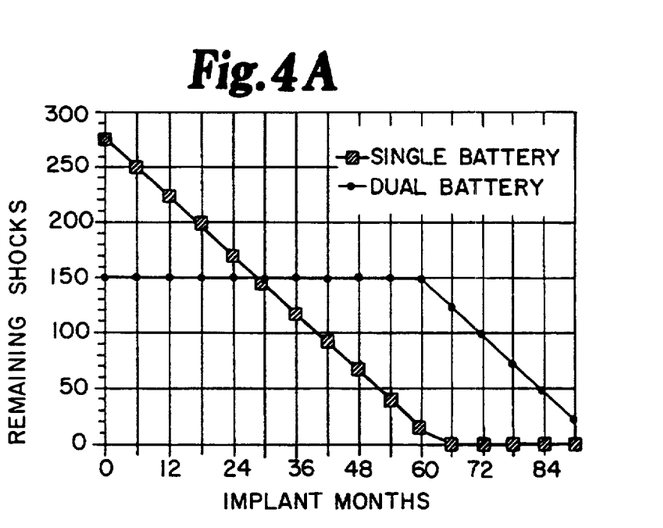
FIGS. 4a, 4b, 4c, 4d and 4e are graphs comparing the predicted lifespan of an implantable cardioverter defibrillator having a single battery system and a dual battery power system.

In FIG. 4a, the graph shows a comparison of the devices under an assumption that the device will deliver five maximum defibrillation countershock pulses per month and that pacing is not enabled. It will be noted that in a preferred embodiment of the present invention, the initial number of shocks is 150, as compared with 275 for the other device. It will also be noted, however, that the expected minimum life span of both the single battery system 100 and the present invention 102 are equal at 30 months under these assumptions.

Figure 4B:
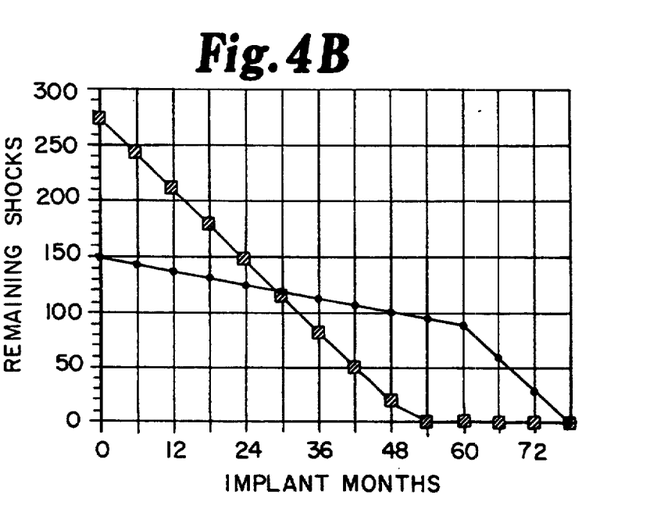

In FIG. 4b, the graph shows a comparison of the devices under an assumption that the device will deliver one defibrillation countershock pulse per month and that pacing is not enabled. In this example, the dual battery system 102 of the present invention has more remaining shocks after 30 months than the single battery system, even though it started with almost one-half the initial number of shocks.

Figure 4C:
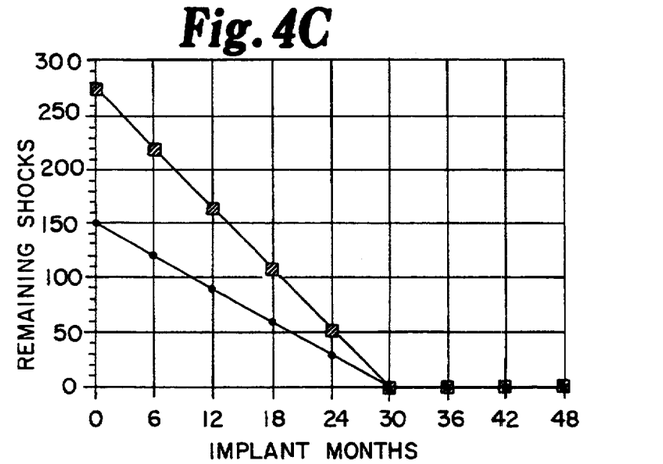

In FIG. 4c, the graph shows a comparison of the devices under an assumption that the device will deliver no defibrillation countershock pulses and that pacing is not enabled. Again, due to the energy drain on the single battery system 100 associated with its monitoring functions, the dual battery system 102 of the present invention provides a longer life span with more average remaining shocks available over that life span. This graph also shows how the energy of the output battery remains relatively the same (i.e., same number of remaining shocks) when no output therapies are delivered.

Figure 4D:
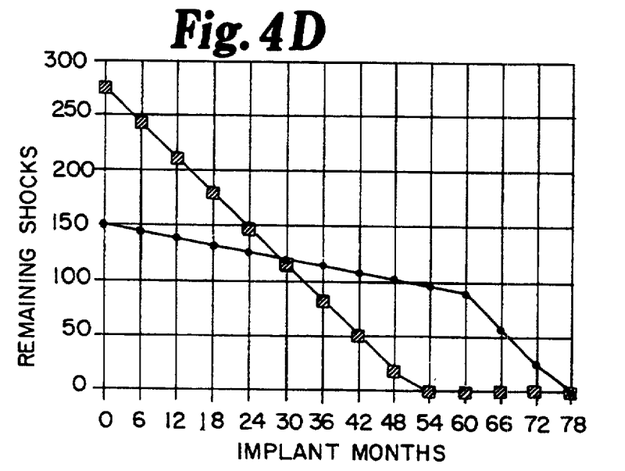

In FIG. 4d, the graph shows a comparison of the devices under an assumption that the device will deliver one defibrillation countershock pulse per month and that pacing is enabled and will be utilized 50% of the time. Again, the dual battery system 102 of the present invention has a longer life span and more average remaining shocks over that life span. It is interesting to note that this situation, the previous dual battery systems described in the background art section would encounter a severe problem. After a period of 50% pacing, all of the energy from the low voltage battery would have been drained, and the device would abruptly stop working, even though there were plenty of shocks remaining in the high voltage battery. It is speculated that this is one of the major reasons why implantable cardioverter defibrillators using the previous dual battery systems were never manufactured.

Figure 4E:
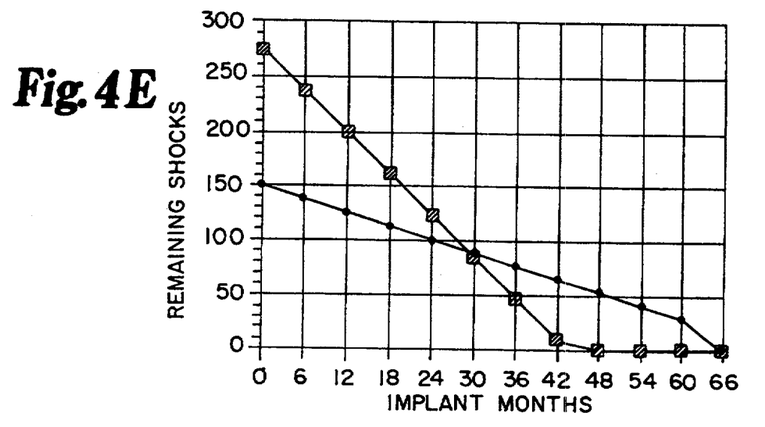

In FIG. 4e, the graph shows a comparison of the devices under an assumption that the device will deliver no defibrillation countershock pulses and that pacing is enabled and will be utilized 50% of the time. Once again the dual battery system 102 of the present invention has a longer life span and more average remaining shocks over that life span. As with the problem of the previous dual battery systems described with respect to FIG. 4d, such an end-of-monitoring life problem is even more pronounced in this situation as essentially all of the initial energy of the high voltage battery remains unused in the previous dual battery systems, but the device is "dead" because the low voltage battery is drained of its energy due to the energy requirements of the pacing therapy outputs.

Figure 5A:
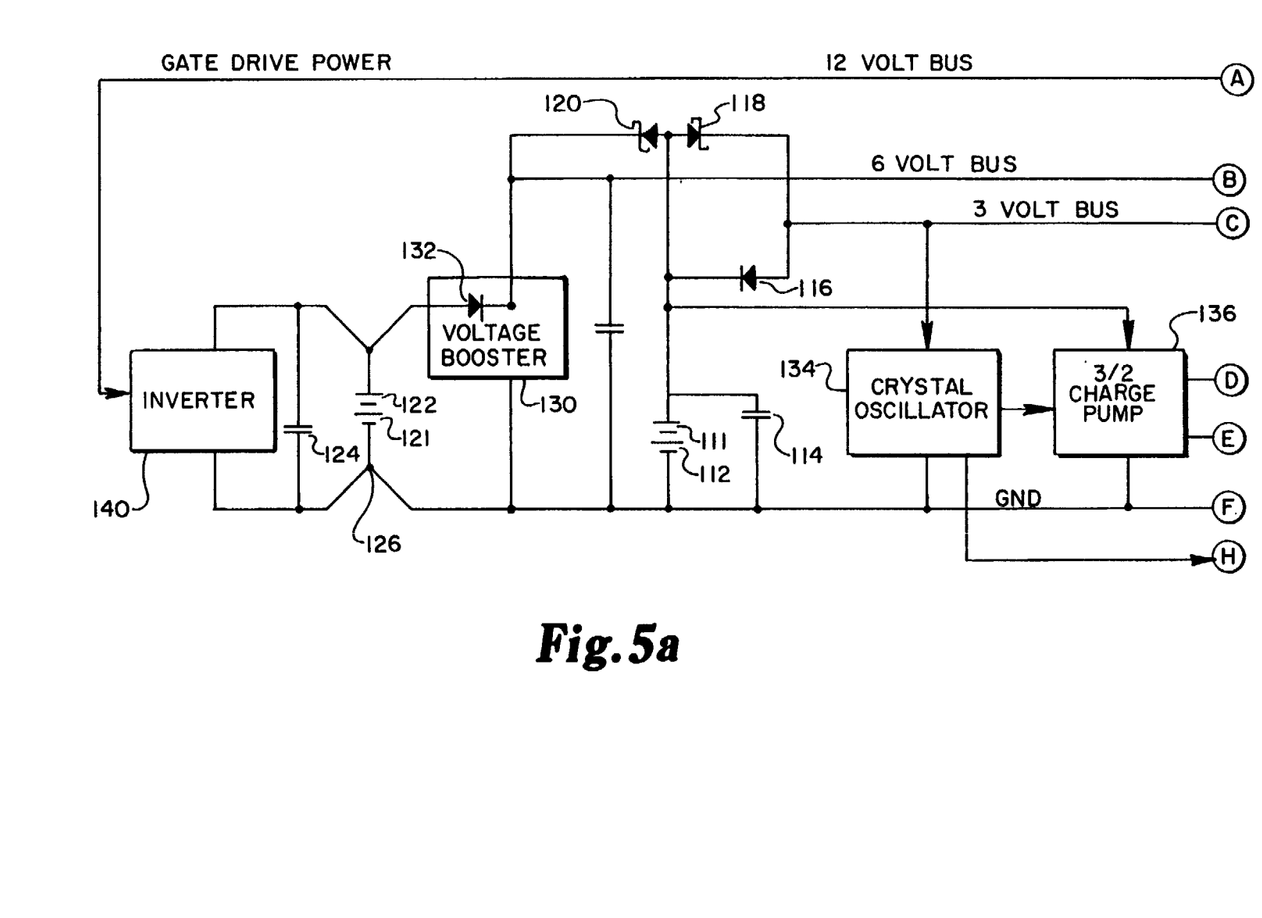
FIGS. 5a and 5b is a schematic diagram of a preferred embodiment of the present invention.
Figure 5B:
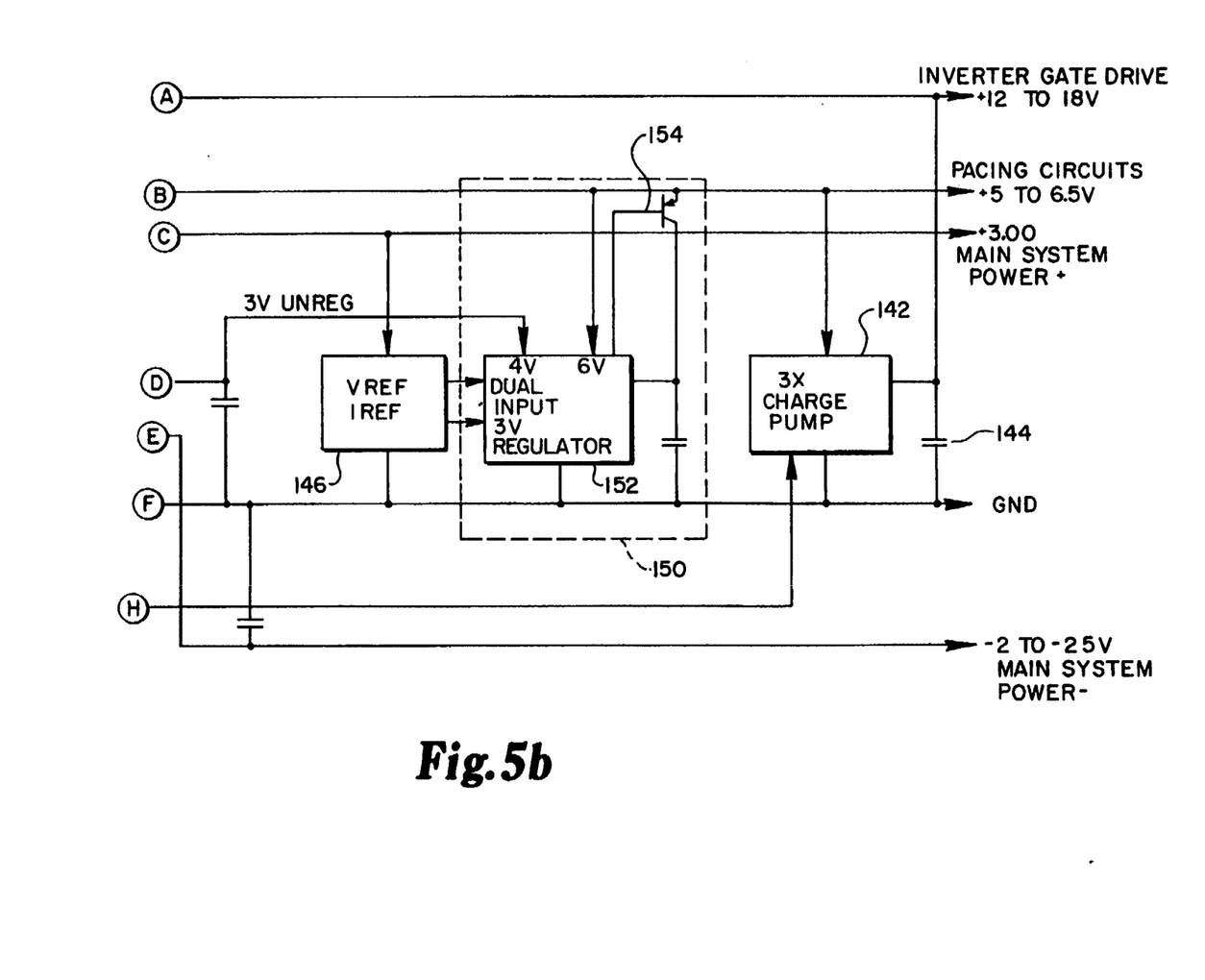

Referring now to FIGS. 5a and 5b, a more detailed explanation of a preferred embodiment of the dual battery power system of the present invention will be described.

A LiI monitoring battery cell 111 provides a low current, low voltage output of about 2.0–2.8 V with a maximum current draw on the order of 30–80 $\mu$A. The output of the monitoring battery cell 111 is capacitively decoupled by a capacitor 114. Schottky diodes 118 and 120 enable the power system to run the 3 V bus from the battery cell 111 during battery startup sequencing such that the device can be successfully initiated by first inserting the monitoring battery cell 111 before the output batteries are inserted.

A pair of $LiAgV_2O_5$ output battery cells 121, 122 provide a relatively high current, high voltage output of 4.0 to 6.5 V with a maximum current draw of between about 2.0–4.0 A. The high current output of the output battery cells 121, 122 is capacitively decoupled by a capacitor 124. A center point ground 126 isolates the high current portion of the circuitry from the low current portion of the circuitry, thereby allowing for simpler circuit design and greater reliability of the low current portion of the circuitry. A voltage booster 130 insures a 6 V supply on the 6 Volt Bus, even while the output battery cells 121, 122 are under heavy load conditions, while the diode 132 in the voltage booster 130 isolates the boosted voltage from the battery cell voltage during periods of high current draw.

An inverter circuit 140 uses the high current output and an Inverter Gate Drive Voltage of 12 to 18 volts provided by a 3X charge pump circuit 142 from the 6 Volt Bus to drive a high-voltage flyback transformer in the inverter circuit 140. The output of the transformer charges a capacitor system (not shown) to produce the high voltage (50–800 V) capacitive discharge output pulse which forms either a cardioversion or defibrillation pulse countershock. The Inverter Gate Drive Voltage is capacitively decoupled by capacitor 144. The inverter circuit 140 may be of the type described, for example, in U.S. Pat. No. 4,800,883.

The Main System Power is a regulated 3.0 V supplied primarily by the monitoring battery cell 111 unless the current draw on the Main System Power exceeds about 30–80 $\mu$A. In the event of a current overdraw situation, such as when the microprocessor in inverter/output circuitry 38 responds to a wake-up condition, the output of the output battery cells 121, 122 is added to the output of the monitoring battery cell 111 to generate the required current. The circuitry to accomplish this is shown generally at 150 and is described in greater detail in connection with the description of FIG. 6.

The unregulated 2.5 V output of the monitoring battery cell 111 is supplied as an input to a 3/2 charge pump 136 which, like the 3X charge pump circuit 142, is driven by a 1 KHz divider output of a 32 KHz oscillator crystal 134. The charge pump circuit 136 raises the output of the monitoring batteries to about 3.75 V which is capacitively decoupled by capacitor 146. The 3.75 V output of the charge pump circuit 136 and the unregulated 6.0 Volt Bus are fed as inputs to a dual input voltage regulator 152. A voltage/current reference circuit 146 provides a reference voltage of 1.28 V and a reference current of 100 nA to the voltage regulator 152. A p-n-p transistor 154 controls whether the 6.0 Volt Bus input will be added to the 3.75 V output of the charge pump circuit 136 if a current overdraw condition exists with respect to the monitoring battery cell 111. The charge pump circuit 136 also provides a negative output of −2.0 to −2.5 V to supply the Main Power System negative voltage requirements for op amps, etc.

Figure 6:
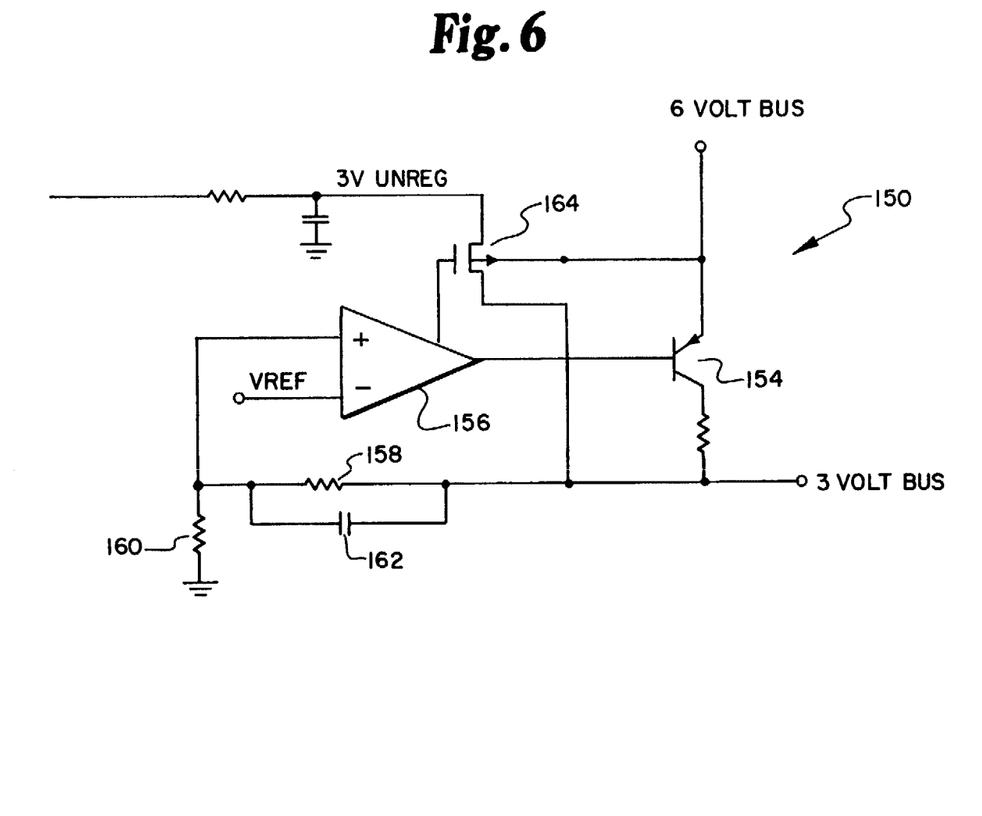
FIG. 6 is a detailed schematic diagram of the backup feature of the embodiment of the present invention shown in FIGS. 5a and 5b.

Referring now to FIG. 6, a more detailed explanation of the operation of the backup feature of a preferred embodiment of the present invention is shown. A feedback amplifier circuit 156 compares the reference voltage signal from the voltage/current reference circuit 146 to a divided down value of the 3 Volt Bus signal. The divide down is accomplished by resistors 158 and 160 and capacitor 162. A FET transistor circuit 164 responds to an output of the feedback amplifier circuit 156 to keep the voltage on the 3 Volt Bus at 3.0 V. If the current drain through the gate of the FET transistor circuit 164 is more than the maximum current draw for the monitoring battery cell 111, then the transistor circuit 154 is turned on by feedback amplifier circuit 156 to supply the necessary overdraw current from the output battery cells 121, 122 via the 6 Volt Bus. In the preferred embodiment, a local feedback loop is added to transistor circuit 154 to sin-relate a quasi-complementary darlington circuit in order to achieve a low drop voltage across transistor circuit 154.

Figure 7:
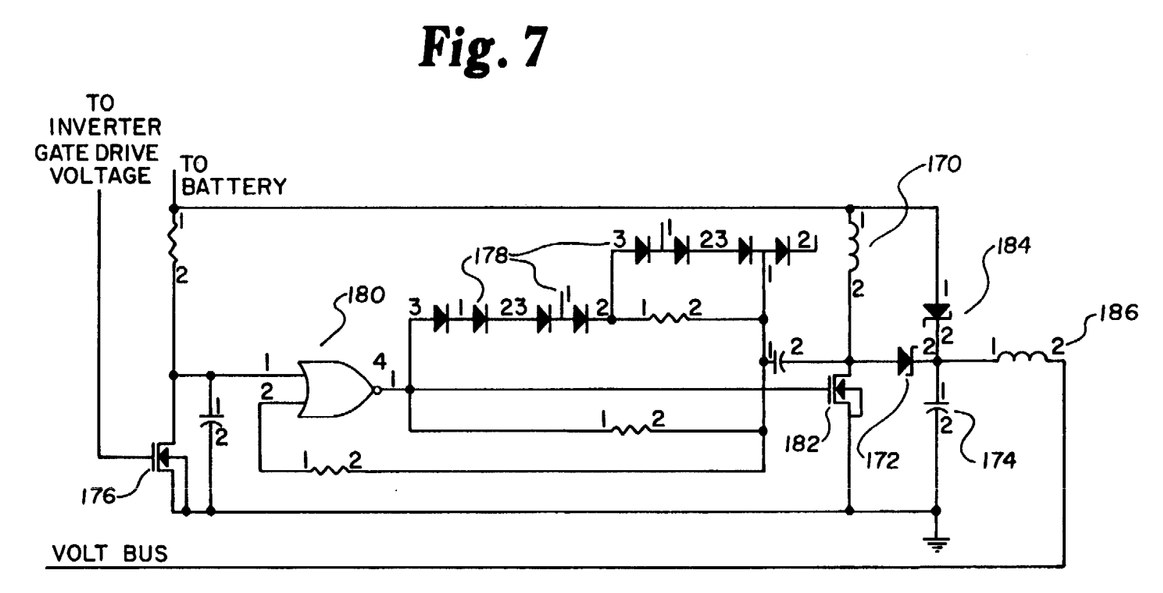
FIG. 7 is a detailed schematic diagram of the booster feature of the embodiment of the present invention shown in FIGS. 5a and 5b.

Referring now to FIG. 7, a more detailed explanation of the operation of the booster feature of a preferred embodiment of the present invention is shown. Voltage supply ripple is caused by changes in the battery impedance due to the high current draw required by the flyback charging operation of inverter circuit 140. If the drop out voltage of the voltage supply is too great, or if the power supply rejection ratio of monitoring circuitry 34 and output circuitry 38 is exceeded. The result may be either local or catostrophic circuit failure. To prevent voltage supply ripple from affecting the voltage supply of the preferred embodiment of the present invention, a voltage booster 130 is used.

The voltage booster 130 of the preferred embodiment as shown in FIG. 7 runs the battery output current through an inductor 170 for a period of time, and then switches the current through a zener diode 172 to a capacitor 174 and to ground. Zener diode 172 regulates the voltage on capacitor 174 and also blocks capacitor 174 from creating ripple in the voltage supply ($V_{DD}$). Voltage booster 130 senses activity by inverter circuit 140 using a FET transistor 176 and begins cycling inductor 170 in accordance with the delays generated by diodes 178 in response to the value of the voltage supply ($V_{DD}$) and the switching of logic gate 180 and FET transistor 182. In this way, voltage booster 130 may efficiently adjust its cycle time to immedialy match the various levels of the voltage supply ($V_{DD}$) that may be encountered during the charging operation. In the preferred embodiment, voltage booster 130 runs at a fixed frequency with a variable duty cycle dependent upon the output voltage of the battery. When voltage booster 130 is not active, current from the output of the battery is routed through Schottky diode 184 and through a choke inductor 186 to the voltage supply ($V_{DD}$).

We claim:

1. An improved power system for an implantable cardioverter defibrillator that is a self-contained human implantable device having monitoring means for detecting myocardial arrhythmias in a human patient and output means for selectively determining an appropriate electrical pulse therapy to be delivered in response to a myocardial arrhythmia detected by the monitoring means and delivering the appropriate electrical pulse therapy to two or more implanted electrodes, the improved power system comprising:
   first battery means for providing electrical power primarily to the monitoring means;
   second battery means for providing substantially all of its electrical power to the output means; and
   backup means for allowing the second battery means to provide electrical power to the monitoring means in the event that the first battery means can no longer provide electrical power to the monitoring means.

2. The improved power system of claim 1 wherein the implantable cardivoerter defibrillator includes a capacitor means for storing an electrical charge which is charged from the second battery means and wherein the output means selects the appropriate electrical pulse therapy from a set that includes:
   one or more cardioversion/defibrillation pulses, each cardioversion/defibrillation pulse being delivered by the output means as a capacitive discharge pulse from the capacitor means; and
   one or more pacing pulses, each pulse being delivered by the output means as an electrical pulse directly powered from the second battery means.

3. The improved power system of claim 1 wherein the backup means comprises:
   transistor means operably connected to outputs of the first battery means and the second battery means to sense a current drain on the output of the first battery means and switch on the output of the second battery means to add to the output of the first battery means in the event that the current drain exceeds a maximum current drain of the first battery means.

4. The improved power system of claim 1 further including:
   voltage regulation means operably connected to an output of the first battery means and to a reference voltage value for regulating the output of the first battery means to a predetermined voltage value.

5. The improved power system of claim 1 wherein the first battery means is a relatively low current source, and wherein the second battery means is a relatively high current source.

6. The improved power system of claim 5, wherein the relatively low current source is a 1.5 to 3.0 volt battery and the relatively high current source is a 6 to 18 volt battery.

7. The improved power system of claim 1 wherein the first battery means is one or more lithium iodide battery cells.

8. The improved power system of claim 1 wherein said second battery means is one or more battery cells selected from the group consisting of:
   lithium silver vanadium oxides, thionyl chlorides or rechargeable battery cells.

* * * * *